United States Patent [19]

Lantzsch et al.

[11] Patent Number: 4,681,952
[45] Date of Patent: Jul. 21, 1987

[54] INTERMEDIATES IN THE PREPARATION OF 2,2-DIMETHYL-3-ARYL-CYCLO-PROPANECARBOXYLIC ACIDS AND ESTERS

[75] Inventors: Reinhard Lantzsch, Leverkusen; Dieter Arlt, Cologne; Manfred Jautelat, Burscheid, all of Fed. Rep. of Germany

[73] Assignee: Bayer Aktiengesellschaft, Leverkusen, Fed. Rep. of Germany

[21] Appl. No.: 669,182

[22] Filed: Nov. 7, 1984

Related U.S. Application Data

[62] Division of Ser. No. 496,719, May 20, 1983, abandoned.

[51] Int. Cl.$^4$ .................. C07D 333/38; C07D 333/37; C07D 333/16; C07D 307/02
[52] U.S. Cl. ........................................ 549/61; 549/62; 549/78; 549/474; 549/498; 556/465; 558/414; 568/305; 568/306; 568/316; 568/323; 568/328; 568/348
[58] Field of Search ............... 568/348, 316, 323, 305, 568/306, 328; 556/465; 558/414; 549/61, 62, 78, 474, 498

[56] References Cited

U.S. PATENT DOCUMENTS 4,195,033  3/1980  Punja .................................... 568/348

Primary Examiner—Alan Siegel
Attorney, Agent, or Firm—Sprung, Horn, Kramer & Woods

[57] ABSTRACT

A process for the preparation of 2,2-dimethyl-3-arylcyclopropanecarboxylic acid or ester of the formula

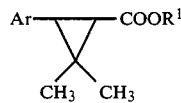

in which
Ar is naphthyl or the radical

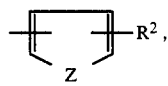

$R^1$ is H or $C_1$–$C_4$-alkyl,
Z is oxygen, sulphur, or 1,2-ethenediyl, and
$R^2$ represents hydrogen, halogen, cyano, nitro or trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy,
comprising reacting a 1-aryl-1-halogeno-2,2-dimethyl-3-butanone of the formula

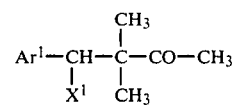

in which
$X^1$ is chlorine or bromine, with a base in the presence of a diluent at a temperature between about $-20°$ and $+150°$ C., thereby to form a 2,2-dimethyl-3-arylcyclobutanone of the formula

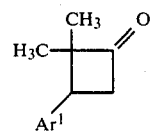

and reacting such 2,2-dimethyl-3-arylcyclobutanone with chlorine or bromine in the presence of an inert diluent at a temperature between about $-30°$ and $+50°$ C., reacting such 2,2-dimethyl-3-arylcyclobutanone with chlorine or bromine in the presence of an inert diluent at a temperature between about $-30°$ and $+150°$ C., thereby to form a 2,2-dimethyl-3-aryl-4-halogenocyclobutanone of the formula

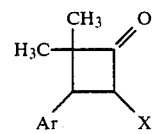

and reacting such 2,2-dimethyl-3-aryl-4-halogenocyclobutanone with an alkali metal alcoholate in the presence of an organic solvent or with an alkali metal or alkaline earth metal hydroxide or carbonate in the presence of water and an organic solvent, at a temperature between about $-20°$ and $+100°$ C. The various intermediates are new and the end product is a known intermediate for known insecticides.

1 Claim, No Drawings

INTERMEDIATES IN THE PREPARATION OF 2,2-DIMETHYL-3-ARYL-CYCLOPROPANECARBOXYLIC ACIDS AND ESTERS

This is a division, of application Ser. No. 496,719, filed May 20, 1983, now abandoned.

The present invention relates to a new process for the preparation of 2,2-dimethyl-3-arylcyclopropanecarboxylic acids, most of which are known, which can be used as intermediate products for the preparation of 2,2-dimethyl-3-arylcyclopropanecarboxylic esters having insecticidal activity, new 2,2-dimethyl-3-aryl-4-halogenocyclobutanones as intermediate products for this purpose and a process for their preparation, and new 2,2-dimethyl-3-arylcyclobutanones as intermediate products for this purpose and a process for their preparation.

It has been disclosed that certain 2,2-dimethyl-3-arylcyclopropanecarboxylic acids are obtained when corresponding 1-aryl-2-methylpropenes are reacted with diazoacetic esters in the presence of catalysts, and the 2,2-dimethyl-3-arylcyclopropanecarboxylic esters formed in this reaction are hydrolyzed (compare: Coll. Czech. Chem. Commun. 25 (1960), 1815). However, this method of synthesis has only a limited range of use. The yields depend greatly on the nature of the aryl radicals and are unsatisfactory in many cases; on reacting 1-thienyl-2-methylpropenes with diazoacetic esters, only decomposition products are obtained. In addition, the use of diazoacetic esters is associated with the known safety risks. Furthermore, the starting materials can mostly only be prepared with difficulty.

Moreover, the synthesis of ethyl 2,2-dimethyl-3-phenylcyclopropanecarboxylate via 4-methyl-3-phenyl-γ-valerolactone has been disclosed (compare Bull. Soc. Chim. France 1961, 1857). However, this route demands a number of precursors, some of which are relatively complicated, and provides only a low yield overall.

2,2-dimethyl-3-phenylcyclopropanecarboxylic esters are also obtained by catalytic hydrogenation of 2,2-dimethyl-3-phenylcyclopropenecarboxylic esters (compare: Chem. Ber. 111 (1978). 3879). However, the synthesis of the 2,2-dimethyl-3-phenylcyclopropenecarboxylic esters required as starting materials takes place via several steps, some of which are very difficult.

Furthermore, 2,2-dimethyl-3-arylcyclopropanecarboxylic esters can also be prepared by reaction of cinnamic esters with triphenylisopropylphosphonium iodide in the presence of strong bases, such as, for example, butyllithium (compare: Japanese Patent Specification No. 8,105,435). However, this process is industrially elaborate and costly.

The present invention relates to:
(1) a process for the preparation of 2,2-dimethyl-3-arylcyclopropanecarboxylic acids (carboxylic esters) of the formula (I)

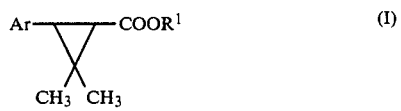

in which
Ar represents naphthyl or the radical

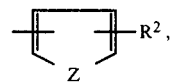

wherein
Z represents oxygen, sulphur or 1,2-ethenediyl. (—CH=CH—),
$R^1$ represents H or $C_1$–$C_4$-alkyl and
$R^2$ represents hydrogen, halogen, cyano, nitro or trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy,
characterized in that 2,2-dimethyl-3-aryl-4-halogenocyclobutanones of the formula (II)

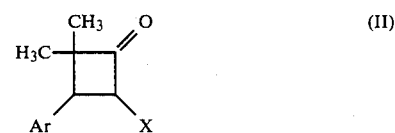

in which
Ar has the abovementioned meaning and
X represents chlorine or bromine, are reacted with bases from the series of alkali metal alcoholates in the presence of organic solvents or alkali metal or alkaline earth metal hydroxides and carbonates in the presence of water and organic solvents, optionally in the presence of catalysts, at temperatures between −20° and +100° C.;

(2) new 2,2-dimethyl-3-aryl-4-halogenocyclobutanones of the formula (II)

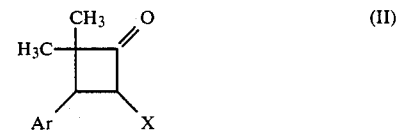

in which
X represents chlorine or bromine and
Ar represents naphthyl or the radical

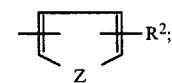

wherein
Z represents oxygen, sulphur or 1,2-ethenediyl (—CH=CH—) and
$R^2$ represents hydrogen, halogen, cyano, nitro or trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy;

(3) a process for the preparation of the new 2,2-dimethyl-3-aryl-4-halogenocyclobutanones of the formula (II) (above), characterized in that 2,2-dimethyl-3-arylcyclobutanones of the formula (III)

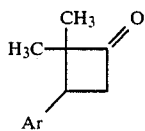

in which
Ar has the abovementioned meaning, are reacted with halogens (chlorine or bromine) in the presence of inert diluents at temperatures between −30° and +50° C.;

(4) new 2,2-dimethyl-3-arylcyclobutanones of the formula (IIIa)

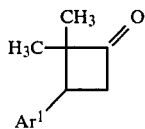

in which
Ar¹ represents naphthyl or the radical

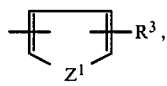

wherein
$Z^1$ represents oxygen, sulphur or 1,2-ethenediyl and
$R^3$ represents a halogen, cyano, nitro or trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy;

(5) a process for the preparation of the new 2,2-dimethyl-3-arylcyclobutanones of the formula (IIIa), characterized in that 1-aryl-1-halogeno-2,2-dimethyl-3-butanones of the formula (IV)

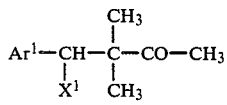

in which
Ar¹ has the abovementioned meaning and
$X^1$ represents chlorine or bromine, are reacted with bases in the presence of diluents at temperatures between −20° and +150° C.

It is surprising that it is possible to prepare 2,2-dimethyl-3-arylcyclopropanecarboxylic esters in good yields starting from 1-aryl-1-halogeno-2,2-dimethyl-3-butanones via the corresponding 2,2-dimethyl-3-arylcyclobutanones and 2,2-dimethyl-3-aryl-4-halogenocyclobutanones, since it is known from the literature that 1-aryl-1-halogeno-2,2-dimethyl-3-butanones with alcohols in the presence of bases form corresponding ethers and react with alkali metal hydroxides in aqueous-organic solution with substitution of the halogen by a hydroxyl group (compare: Arch. Pharm. 308 (1975), 422; ibid. 313 (1980), 795).

The advantages of the process according to the invention are that readily available starting materials can be used, the individual process steps take place smoothly, and that it is generally possible for good yields to be obtained.

If, for example, 2,2,dimethyl-3-(4-fluorophenyl)-4-chlorocyclobutanone and potassium hydroxide are used, as starting components for the preparation of 2,2-dimethyl-3-arylcyclopropanecarboxylic acids (carboxylic esters) in the process set out under 1) above, the process according to the invention can be outlined, using this example, by the following scheme:

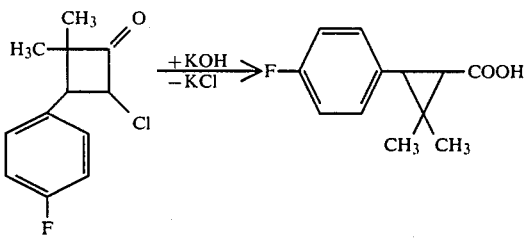

Apart from water, organic solvents are employed to carry out the process according to the invention set out above under 1). Those solvents suitable are preferably, on the one hand, polar and readily miscible with water, such as, for example, acetone, methyl ethyl ketone, methyl isobutyl ketone, acetonitrile, tetrahydrofuran, dioxane and 1,2-dimethoxyethane, or, on the other hand, solvents which are virtually immiscible with water from the series of optionally halogenated hydrocarbons, such as, for example, hexane, cyclohexane, heptane, petroleum ether, ligroin, methylene chloride, chloroform, benzene, toluene and xylene.

In addition, alcohols can also be employed as solvents, such as, for example, methanol, ethanol, isopropanol and tert.-butanol.

When using solvents which are virtually immiscible with water, phase transfer catalysts from the series of tetraalkyl- or trialkylaralkyl-ammonium salts, such as, for example, tetrabutylammonium bromide or triethylbenzylammonium chloride are preferably employed.

The bases employed in the process according to the invention set out above under (1) are alkali metal or alkaline earth metal hydroxides, such as, for example, sodium, potassium, magnesium and calcium hydroxide, alkali metal or alkaline earth metal carbonates, such as, for example, sodium, potassium, magnesium and calcium carbonate or alkali metal alcoholates, such as, for example, sodium or potassium methylate, sodium or potassium ethylate, sodium isopropylate and potassium tert.-butylate.

For the preparation of the acids, alkali metal hydroxides, such as, for example, sodium hydroxide or potassium hydroxide are preferably employed.

For the preparation of the esters, the alkali metal alcoholates, such as, for example, sodium methylate, sodium ethylate, sodium isopropylate and potassium tert.-butylate are preferably employed. The corresponding alcohols are then preferably used as the solvent.

On carrying out the process according to the invention, the reaction temperatures are generally maintained between −20° and +100° C., preferably between +10° and +50° C.

The process according to the invention is generally carried under normal pressure.

In order to carry out the process according to the invention, in general 2 to 15 mol-equivalents, preferably 2 to 10 mol-equivalents of a base are employed per mol of 2,2-dimethyl-3-aryl-4-halogenocyclobutanone of the formula (II). In a preferred embodiment of the process according to the invention, the aqueous solution of the base, where appropriate diluted with an organic solvent, is initially introduced and the 2,2-dimethyl-3-aryl-4-halogenocyclobutanone of the formula (II), where appropriate dissolved in an organic solvent, and, where appropriate, a catalyst are added to the former. The reaction mixture is stirred until the reaction has ended and worked up in a conventional manner, for example by acidification and extraction with methylene chloride. The product of the formula (I) is obtained after distilling off the organic extracting agent as a crystalline residue.

The new 2,2-dimethyl-3-aryl-4-halogenocyclobutanones to be used as intermediate products in the process according to the invention are generally defined by the formula (II) above under (2).

In this formula:

X preferably represents chlorine or bromine and
Ar preferably represents naphthyl or the radical

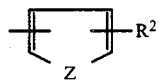

wherein

Z represents oxygen, sulphur or 1,2-ethenediyl (—CH=CH—) and $R^2$ represents hydrogen, fluorine, chlorine, bromine, cyano, nitro or trimethylsilyl or a radical, which is optionally substituted by fluorine and/or chlorine, from the series comprising $C_1$–$C_6$-alkyl, $C_3$–$C_6$-cycloalkyl, $C_2$–$C_6$-alkenyl, $C_1$–$C_4$-alkoxy, $C_1$–$C_2$-alkylenedioxy, $C_1$–$C_4$-alkylthio, $C_1$–$C_4$-alkylsulphinyl, $C_1$–$C_4$-alkylsulphonyl, di-$C_1$–$C_4$-alkylamino, phenyl and phenoxy.

The compounds of the formula (II) are particularly preferred in which

X represents chlorine or bromine and
Ar represents phenyl which is optionally substituted in the meta and/or para position by fluorine, chlorine, bromine, $C_1$–$C_4$-alkyl, trifluoromethyl, methoxy, trifluoromethoxy, methylenedioxy or difluoromethylenedioxy.

Examples of the new compounds of the formula (I) which may be mentioned are: 2,2-dimethyl-3-phenyl-, -3-(4-fluorophenyl)-, -3-(4-chlorophenyl-, -3-(4-methylphenyl)-, -3-(4-tert.-butylphenyl)-, -3-(4-trifluoromethylphenyl)-, -3-(4-methoxyphenyl)- and -3-(4-trifluoromethoxyphenyl)-4-chorocyclobutanone and 2,2-dimethyl-3-phenyl-, -3-(4-fluorophenyl)-, -3-(4-chlorophenyl)-, -3-(4-methylphenyl)-, -3-(4-tert.-butylphenyl)-, -3-(4-trifluoromethylphenyl)-, -3-(4-methoxyphenyl)- and -3-(4-trifluoromethoxyphenyl)-4-bromocyclobutanone.

If, for example, 2,2-dimethyl-3-(4-fluorophenyl)cyclobutanone and chlorine are used as starting materials for the preparation of the new 2,2-dimethyl-3-aryl-4-halogenocyclobutanones of the formula (II) in the process set out above under (3), their reaction according to the invention can be outlined by the following scheme:

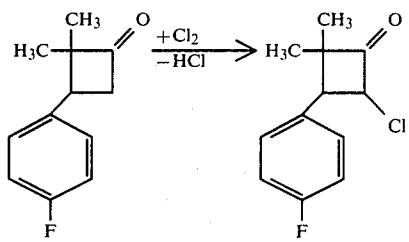

The process according to the invention set out under (3) is carried out using inert diluents. Suitable as such are preferably halogenated hydrocarbons, such as, for example, methylene chloride, chloroform, dichlorodifluoromethane, tetrachloromethane and ethylene chloride and, where appropriate, also carboxylic acids, such as, for example, acetic acid.

The reaction is carried out at temperature between $-30°$ C. and $+50°$ C., preferably at $0°$ C. to $+30°$ C. and, in general, under normal pressure.

In general, 0.8 to 1.2 mols, preferably 0.9 to 1 mol, of chlorine or bromine is employed per 1 mol of 2,2-dimethyl-3-arylcyclobutanone of the formula (III).

In a preferred embodiment of the process set out under (3), a solution of the 2,2-dimethyl-3-arylcyclobutanone is initially introduced and the halogen is slowly metered in in the form of a gas or in solution. After the reaction has ended, the product of the formula (II) is isolated by distilling off the solvent.

The 2,2-dimethyl-3-arylcyclobutanones required as intermediate products are generally defined by the formula (III) above under (3). In this formula, the radicals Ar and X preferably or particularly preferably have the same meanings as are given in the definition of the corresponding radicals Ar and X in formula (II) as being "preferred" or "particularly preferred" respectively.

2,2-Dimethyl-3-phenylcyclobutanone may be mentioned as a compound already known (compare: Angew. Chem. 75 (1963), 841; ibid. 93 (1981), 931).

The new 2,2-dimethyl-3-arylcyclobutanones are defined by formula (IIIa) above under (4). In this formula:

$Ar^1$ preferably represents naphthyl or the radical

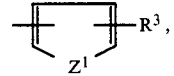

wherein $Z^1$ represents oxygen, sulphur or 1,2-ethenediyl and
$R^3$ represents fluorine, chlorine, bromine, cyano, nitro or trimethylsilyl or radicals, which are optionally substituted by fluorine and/or chlorine, from the series comprising $C_1$–$C_6$-alkyl, $C_3$–$C_6$-cycloalkyl, $C_2$–$C_6$-alkenyl, $C_1$–$C_4$-alkoxy, $C_1$–$C_2$-alkylenedioxy, $C_1$–$C_4$-alkylthio, $C_1$–$C_4$-alkylsulphinyl, $C_1$–$C_4$-alkylsulphonyl, di-$C_1$–$C_4$-alkylamino, phenyl or phenoxy.

New compounds of the formula (IIIa) are particularly preferred in which $Ar^1$ represents phenyl substituted in the meta and/or para position by radicals from the series comprising fluorine, chlorine, bromine, $C_1$–$C_4$-alkyl, trifluoromethyl, methoxy, trifluoromethoxy, methylenedioxy or difluoromethylenedioxy.

Examples of new compounds of the formula (IIIa) which may be mentioned are: 2,2-dimethyl-3-(4-fluorophenyl)-, -3-(4-chlorophenyl)-, -3-(4-methylphenyl)-, -3-(4-trifluoromethylphenyl)-, -3-(4-tert.-butylphenyl)-, -3-(4-methoxyphenyl)- and -3-(4-trifluoromethoxyphenyl)cyclobutanone.

If, for example, 1-(4-fluorophenyl)-1-chloro-2,2-dimethyl-3-butanone and potassium methanolate are used as starting components for the preparation of the new 2,2-dimethyl-3-arylcyclobutanones of the formula (IIIa) in the process set out above under (5), their reaction according to the invention can be outlined by the following scheme:

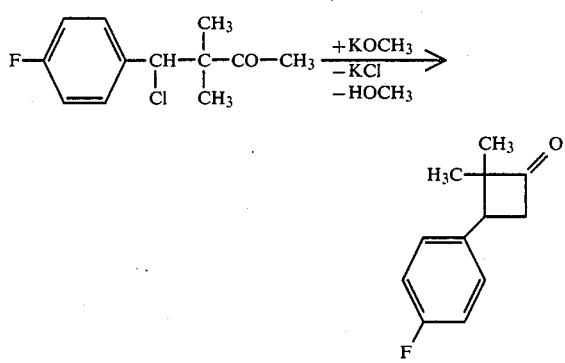

The process according to the invention set out under (5) is carried out using diluents. Suitable as such are the customary organic solvents and, where appropriate, also water mixed with them. Alcohols, such as methanol, ethanol, n- and iso-propanol and n-, iso-, sec.- and tert.-butanol are preferably used as diluents.

Alkali metal and alkaline earth metal hydroxides and alcoholates can be used as bases in the process set out under (5). Preferably, alkali metal alcoholates, such as, for example, sodium methanolate and ethanolate or potassium methanolate, ethanolate and tert.-butanolate are employed.

The reaction is generally carried out at temperatures between −20° and +150° C., preferably at 0° to +100° C. and generally under normal pressure.

In general, between 1 and 2 mol-equivalents, preferably between 1 and 1.2 mol-equivalents, of the base to be used is employed per 1 mol of 1-aryl-1-halogeno-2,2-dimethyl-3-butanone of the formula (IV).

In a preferred embodiment of the process set out under (5), the base is initially introduced in solution and a solution of the 1-aryl-1-halogeno-2,2-dimethyl-3-butanone is slowly added to the latter. After the reaction has ended, working up is by customary methods, for example by diluting the reaction mixture with water, neutralizing, extracting with a solvent which is virtually immiscible with water, such as, for example, methylene chloride, drying the extraction solution and filtering, evaporating the filtrate and distilling the residue under high vacuum.

The 1-aryl-1-halogeno-2,2-dimethyl-3-butanones required as intermediate products are generally defined by the formula (IV) above under (5). In formula (IV), the radicals Ar¹ and X¹ preferably or particularly preferably have the same meanings as are given above in the definition of the corresponding radicals Ar¹ and X¹ in formula (IIIa) as being "preferred" or "particularly preferred" respectively.

Examples of compounds of the formula (IV) which may be mentioned are: 1-(4-fluorophenyl)-, 1-(4-chlorophenyl)-, 1-(4-methylphenyl)-, 1-(4-tert.-butylphenyl)-1-(4-trifluoromethylphenyl)-, 1-(4-methoxyphenyl)- and 1-(4-trifluoromethoxyphenyl)-1-chloro-2,2-dimethyl-3-butanone and 1-(4-fluorophenyl)-, 1-(4-chlorophenyl)-, 1-(4-methoxyphenyl)-, 1-(4-tert.-butylphenyl)-, 1-(4-trifluoromethylphenyl)-, 1-(4-methoxyphenyl)- and 1-(4-trifluoromethoxyphenyl)-1-bromo-2,2-dimethyl-3-butanone.

The 1-aryl-1-halogeno-2,2-dimethyl-3-butanones of the formula (IV) are obtained when 1-aryl-2,2-dimethyl-3-butanones of the formula (V)

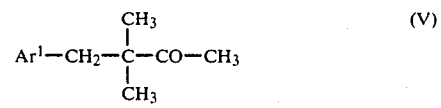

in which

Ar¹ has the abovementioned meaning, are reacted, in the presence of an inert diluent, such as, for example, tetrachloromethane, and in the presence of a catalyst, such as, for example, azobisisobutyronitrile. with an agent for radical halogenation, such as, for example, N-bromosuccinimide or N-chlorosuccinimide, at temperatures between 40° and 120° C. The products of the formula (IV) can be isolated in a pure form by distillation under reduced pressure.

The 1-aryl-2,2-dimethyl-3-butanones of the formula (V) required as intermediate products are obtained when arylmethyl halides of the formula (VI)

$$Ar^1-CH_2-X^2 \qquad (VI)$$

in which

Ar¹ has the abovementioned meaning and

X represents halogen, preferably chlorine, are reacted with methyl isopropyl ketone in the presence of a base, such as, for example, potassium hydroxide, in the presence of a diluent, such as, for example, toluene, and in the presence of a phase transfer catalyst, such as, for example, tetrabutylammonium bromide, at temperatures between 20° and 130° C. and, after filtering and washing the reaction mixture, the products of the formula (V) are isolated by distillation undr high vacuum.

The 2,2-dimethyl-3-arylcyclopropanecarboxylic acids of the formula (I) to be prepared by the process according to the invention can be used as intermediate products for the preparation of 2,2-dimethyl-3-arylcyclopropanecarboxylic esters having insecticidal activity (compare Coll. Czech. Chem. Commun. 25 (1960), 1815).

PREPARATION EXAMPLES

Example 1

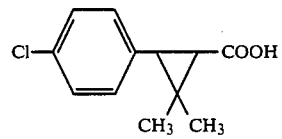

2.6 g of 2,2-dimethyl-3-(4-chlorophenyl)-4-bromocyclobutanone (for preparation of the crude product, see Example 2) are dissolved in 10 ml of dioxane and this solution is added dropwise to a solution of 2 g of sodium hydroxide in 20 ml of water and 10 ml of dioxane. The reaction mixture is stirred at 20° C. for 5 minutes and extracted with methylene chloride. After acidification of the aqueous phase, it is again extracted with methylene chloride. After distilling off the solvent from the combined extraction solutions, 1.1 g of 2,2-dimethyl-3-(4-chlorophenyl)cyclopropanecarboxylic acid of melting 115° C. is obtained.

Example 2

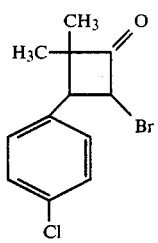

2.08 g (0.01 mol) of 2,2-dimethyl-3-(4-chlorophenyl)-cyclobutanone are dissolved in 30 ml of chloroform, and a solution of 1.6 g of bromine in 5 ml of chloroform is added dropwise. After stirring for one hour at 20° C., the solvent is distilled off under waterpump vacuum. 2.6 g of crude 2,2-dimethyl-3-(4-chlorophenyl)-4-bromocyclobutanone are obtained as a residue which is employed further without further purification (compare: Example 1).

Example 3

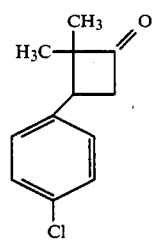

0.91 g (0.04 mol) of sodium is dissolved in 100 ml of ethanol and, at 20° C., 10.5 g (0.036 mol) of 1-bromo-1-(4-chlorophenyl)-2,2-dimethyl-3-butanone in 20 ml of ethanol are added. The reaction mixture is stirred at 20° C. for about 15 hours, diluted with water and neutralized. It is extracted with methylene chloride, dried with sodium sulphate and the solvent is distilled off from the filtrate under waterpump vacuum. The residue is purified by distillation under high vacuum. 4.8 g (65% of theory) of 2,2-dimethyl-3-(4-chlorophenyl)cyclobutanone of boiling point 98° to 107° C./0.05 mbar are obtained.

Example 4

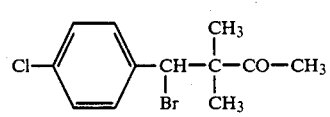

50 g (0.237 mol) of 1-(4-chlorophenyl)-2,2-dimethyl-3-butanone are dissolved in 500 ml of tetrachloromethane, and 44.5 g (0.25 mol) of N-bromosuccinimide and 0.5 g of azobisisobutyronitrile are added. The reaction mixture is heated to boiling under reflux until solid material no longer sinks to the bottom on switching off the stirrer. After cooling down, the succinimide is filtered off with suction, the solvent is distilled off from the filtrate under waterpump vacuum and the residue is distilled under high vacuum. 56.3 g (82% of theory) of 1-(4-chlorophenyl)-1-bromo-2,2-dimethyl-3-butanone of boiling point 112°–118° C./0.2 mbar are obtained.

Example 5

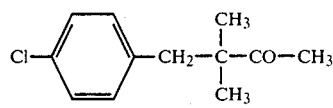

254 g (4 mols) of potassium hydroxide powder (88% pure) are suspended in 1 liter of toluene. To this are slowly added 40 g of tetrabutylammonium bromide and a mixture of 644 g (4 mols) of 4-chlorobenzyl chloride and 430 g (5 mols) of methyl isopropyl ketone at 85° C. The reaction mixture is stirred a further 3 hours at 85° C. After cooling down, it is filtered and the filtrate is washed to neutrality. 732.5 g (87% of theory) of 1-(4-chlorophenyl)-2,2-dimethyl-3-butanone of boiling point 87°–90° C./0.05 mbar are obtained by fractional distillation under high vacuum.

It will be understood that the specification and examples are illustrative but not limitative of the present invention and that other embodiments within the spirit and scope of the invention will suggest themselves to those skilled in the art.

We claim:

1. A process for the preparation of a 2,2-dimethyl-3-arylcyclobutanone of the formula

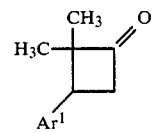

in which
Ar$^1$ is naphthyl or the radical

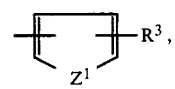

Z$^1$ is oxygen, sulphur or 1,2-ethenediyl, and
R$^3$ is halogen, cyano, nitro or trialkylsilyl or a radical, which is optionally substituted by halogen, from the series comprising alkyl, cycloalkyl, alkenyl, alkoxy, alkylenedioxy, alkylthio, alkylsulphinyl, alkylsulphonyl, dialkylamino, phenyl and phenoxy, comprising reacting a 1-aryl-1-halogeno-2,2-dimethyl-3-butanone of the formula

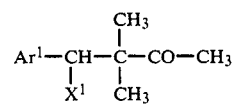

in which
X$^1$ is chlorine or bromine, with about 1 to 1.2 times the molar amount of a base in the presence of a diluent at a temperature between about −20° and +150° C.

* * * * *

UNITED STATES PATENT AND TRADEMARK OFFICE
CERTIFICATE OF CORRECTION

PATENT NO. : 4,681,952

DATED : July 21, 1987

INVENTOR(S) : Reinhard Lantzsch, et al.

It is certified that error appears in the above-identified patent and that said Letters Patent is hereby corrected as shown below:

Title Page, under "[22] Filed"  Insert --[30] FOREIGN APPLICATION PRIORITY DATA June 2, 1982 Fed. Rep. of Germany  32 20 730--

Signed and Sealed this

Fifth Day of April, 1988

Attest:

DONALD J. QUIGG

*Attesting Officer*    *Commissioner of Patents and Trademarks*